United States Patent [19]

Kambin et al.

[11] Patent Number: 5,354,311

[45] Date of Patent: Oct. 11, 1994

[54] DEFLECTING FORCEPS

[75] Inventors: Parviz Kambin, Devon, Pa.; Douglas D. Sjostrom, Wakefield, Mass.

[73] Assignee: Smith & Nephew Dyonics Inc., Memphis, Tenn.

[21] Appl. No.: 117,986

[22] Filed: Sep. 8, 1993

Related U.S. Application Data

[63] Continuation of Ser. No. 737,223, Jul. 29, 1991, abandoned.

[51] Int. Cl.$^5$ .............................................. A61B 17/28
[52] U.S. Cl. ...................................... 606/205; 606/170; 128/751; 128/752; 604/22
[58] Field of Search ............................... 606/205–207, 606/210, 170, 46, 47, 51, 52; 604/22; 128/751, 752

[56] References Cited

U.S. PATENT DOCUMENTS

| | | |
|---|---|---|
| 2,751,908 | 6/1956 | Wallace . |
| 2,790,437 | 4/1957 | Moore . |
| 3,807,406 | 4/1974 | Rafferty et al. . |
| 3,895,636 | 7/1975 | Schmidt . |
| 3,916,909 | 11/1975 | Kletschka et al. . |
| 3,924,608 | 12/1975 | Mitsui . |
| 4,084,594 | 4/1978 | Mosior . |
| 4,372,295 | 2/1983 | Heckele . |
| 4,522,206 | 6/1985 | Whipple et al. . |
| 4,646,751 | 3/1987 | Maslanka . |
| 4,653,476 | 3/1987 | Bonnett . |
| 4,656,999 | 4/1987 | Storz . |
| 4,662,371 | 5/1987 | Whipple et al. . |
| 4,669,471 | 6/1987 | Hayashi . |
| 4,686,965 | 8/1987 | Bonnett et al. . |
| 4,763,668 | 8/1988 | Macek et al. . |
| 4,994,024 | 2/1991 | Falk . |
| 5,209,747 | 5/1993 | Knoepfler . |

FOREIGN PATENT DOCUMENTS

| | | |
|---|---|---|
| 0288309 | 10/1988 | European Pat. Off. . |
| 2748057 | 5/1979 | Fed. Rep. of Germany . |
| 3526822 | 2/1987 | Fed. Rep. of Germany . |
| 3641935 | 6/1987 | Fed. Rep. of Germany ...... 606/205 |
| 8914196 | 3/1990 | Fed. Rep. of Germany . |
| 3923851 | 8/1990 | Fed. Rep. of Germany . |
| 2004749 | 4/1979 | United Kingdom . |

*Primary Examiner*—Michael H. Thaler
*Attorney, Agent, or Firm*—Pravel, Hewitt, Kimball & Krieger

[57] ABSTRACT

A forceps having forceps jaws operated by manually operable handle also has a cable connected between the forceps jaws and a manually operable actuator such that the forceps jaws are swung to a desired position when the actuator is operated.

10 Claims, 4 Drawing Sheets

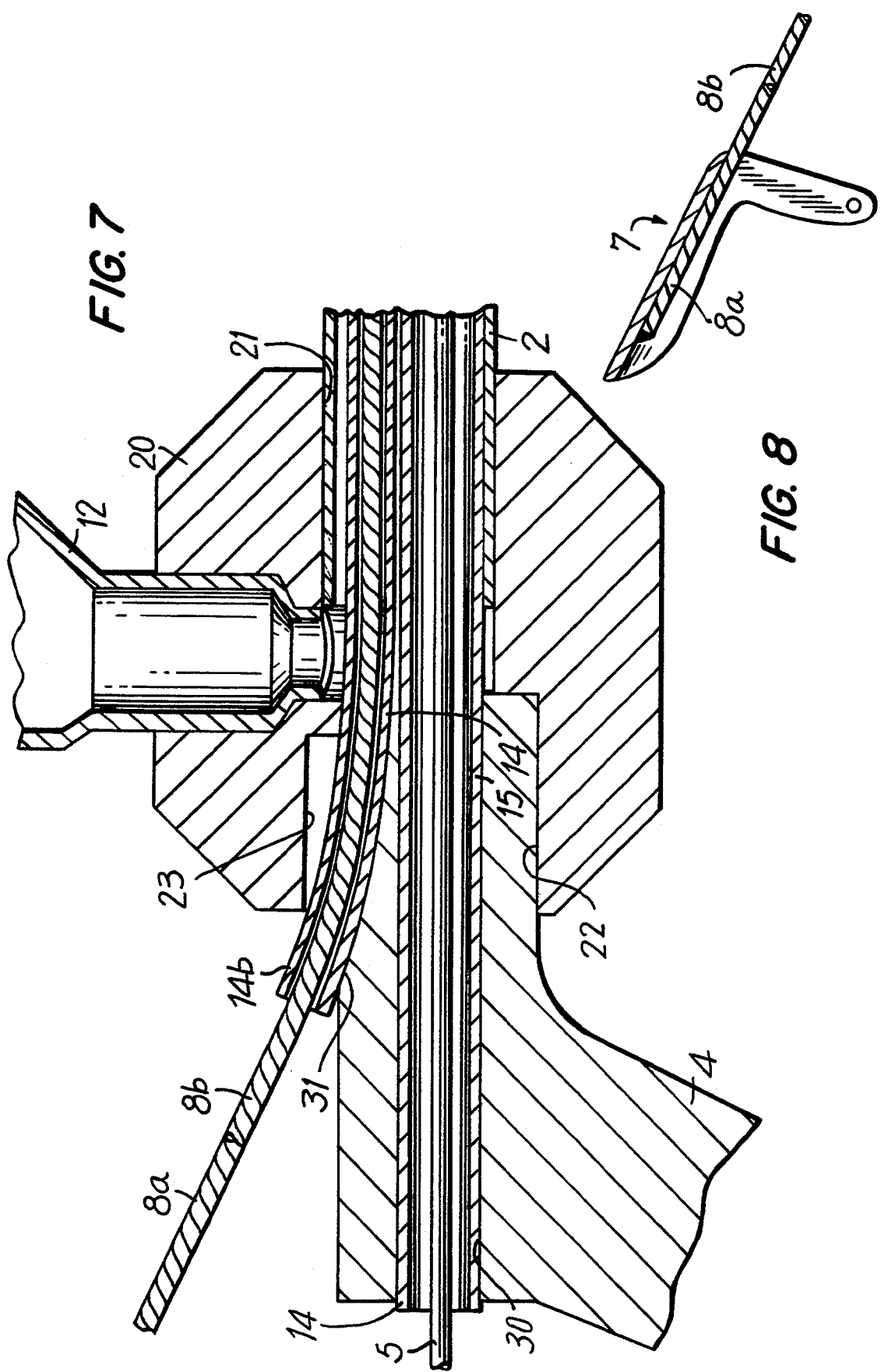

DEFLECTING FORCEPS

This is a continuation of co-pending application Ser. No. 07/737,223 filed on Jul. 29, 1991, now abandoned.

The present invention relates to a deflecting forceps having forceps jaws that can be swung to reach tissue at a location remote from the normal position of the forceps jaws.

While generally useful in surgical procedures, such as endoscopic procedures, the present invention is particularly useful in the procedure described in Parviz Kambin U.S. Pat. No. 4,573,448, issued Mar. 4, 1989, which is incorporated herein by reference thereto. In that procedure, an access cannula is inserted into a herniated intervertebral disc, and thereafter fragments of tissue are removed from the disc through the access cannula. The area that is accessible to surgical tools inserted into the disc through the cannula is limited to tissue lying along a path coaxial with the longitudinal axis of the access cannula. While such surgical tools can be rotated about this axis, they cannot reach tissue located at a position remote from this axis.

The deflecting forceps of the invention provide a means for reaching tissue at these remote locations, since the forceps jaws can be swung from a normal position parallel to or lying along the axis of the cannula to a position transverse to the axis. Tissue located away from the axis can be readily reached and removed, whereas it would have been left untouched by conventional forceps.

In particular, the present invention provides a forceps having forceps jaws extending beyond the distal end of a tubular housing, the jaws being operated by manually operable handles at the proximal end of the housing. The forceps of the invention also includes a cable for swinging the jaws from a first or normal position in which the jaws extend in a direction parallel to the longitudinal axis of the housing to a second position in which the jaws are transverse to the longitudinal axis, and a manually operable actuator at the proximal end of the housing connected to the proximal end of the cable so that the cable can be moved in a direction to swing the jaws to the second position when the actuator is operated.

Preferably, the forceps are provided with a suction conduit communicating the interior of the housing to a source of suction to facilitate removal of tissue by pulling tissue by suction to the forceps jaws. In addition, smaller bits of tissue can be removed from the surgical site by being aspirated through the housing.

The present invention is illustrated in terms of a preferred embodiment in the accompanying drawings, in which.

Figure 1:
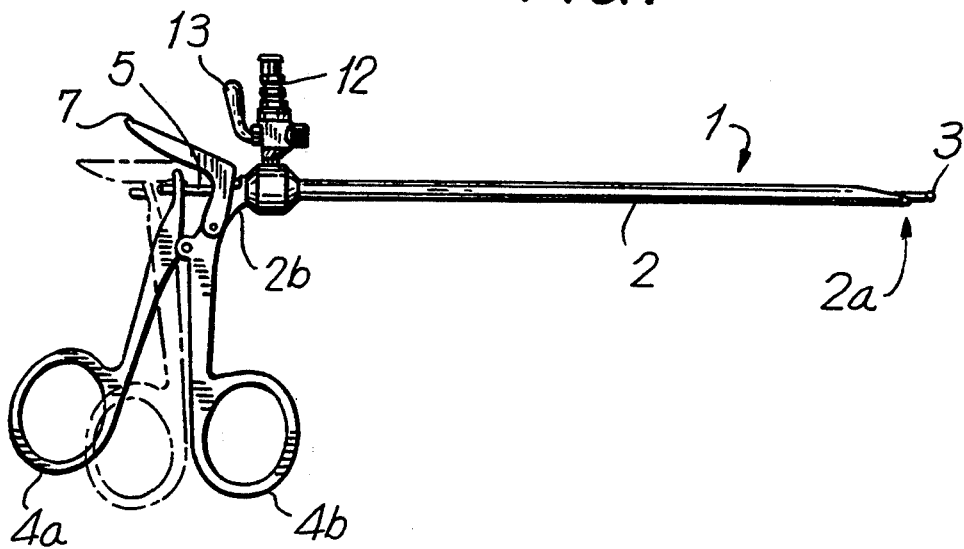
FIG. 1 is an elevational view of an embodiment of the forceps of the invention.
Figure 4:
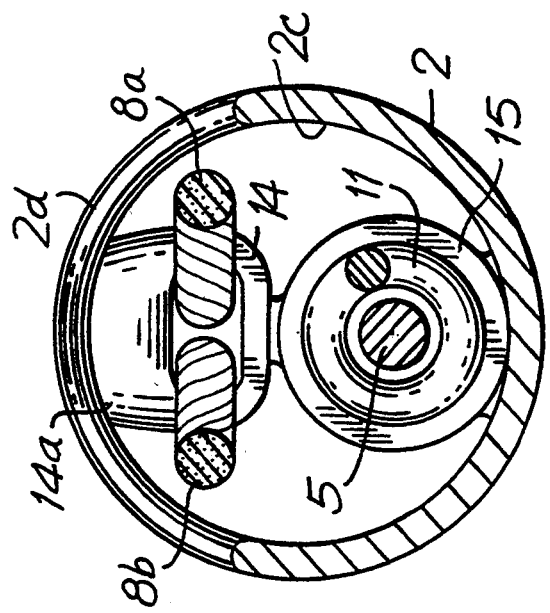
Figure 3:
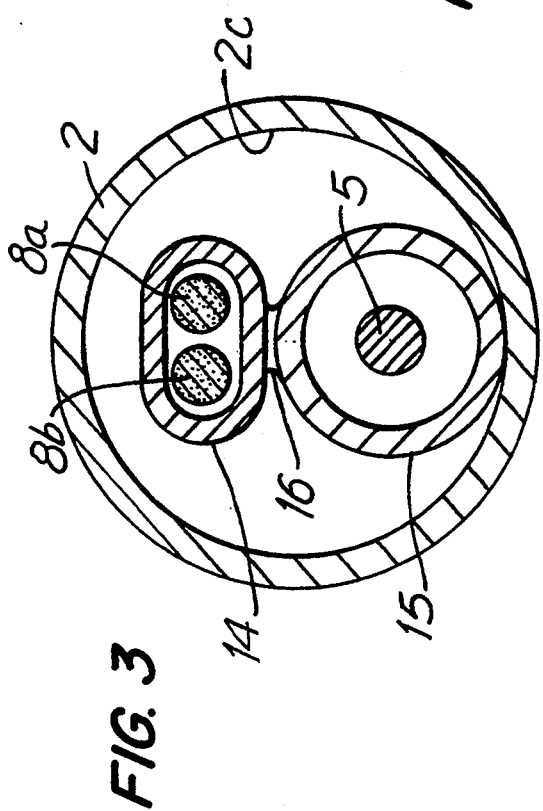

FIGS. 3 and 4 are sections taken along lines 3—3 and 4—4 in FIG. 1, respectively.

Figure 6:
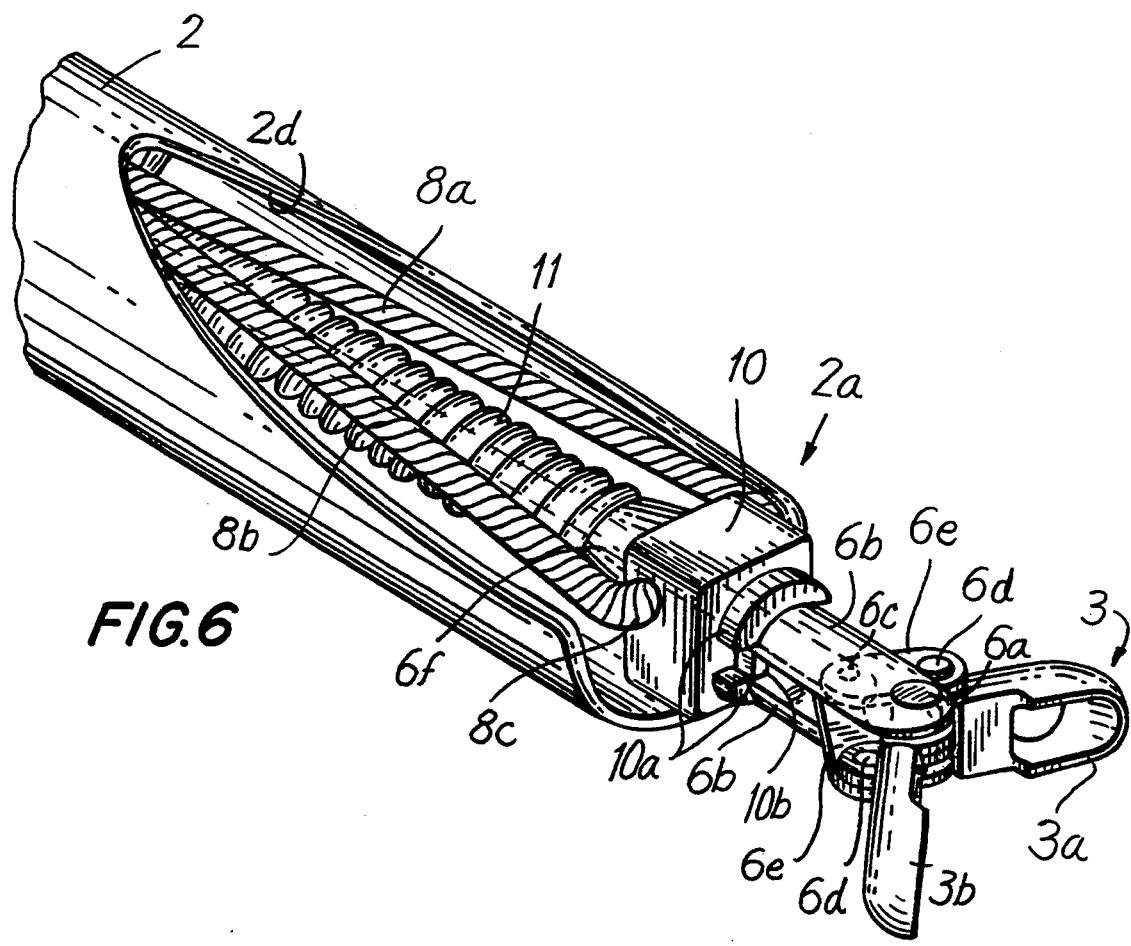
Figure 5:
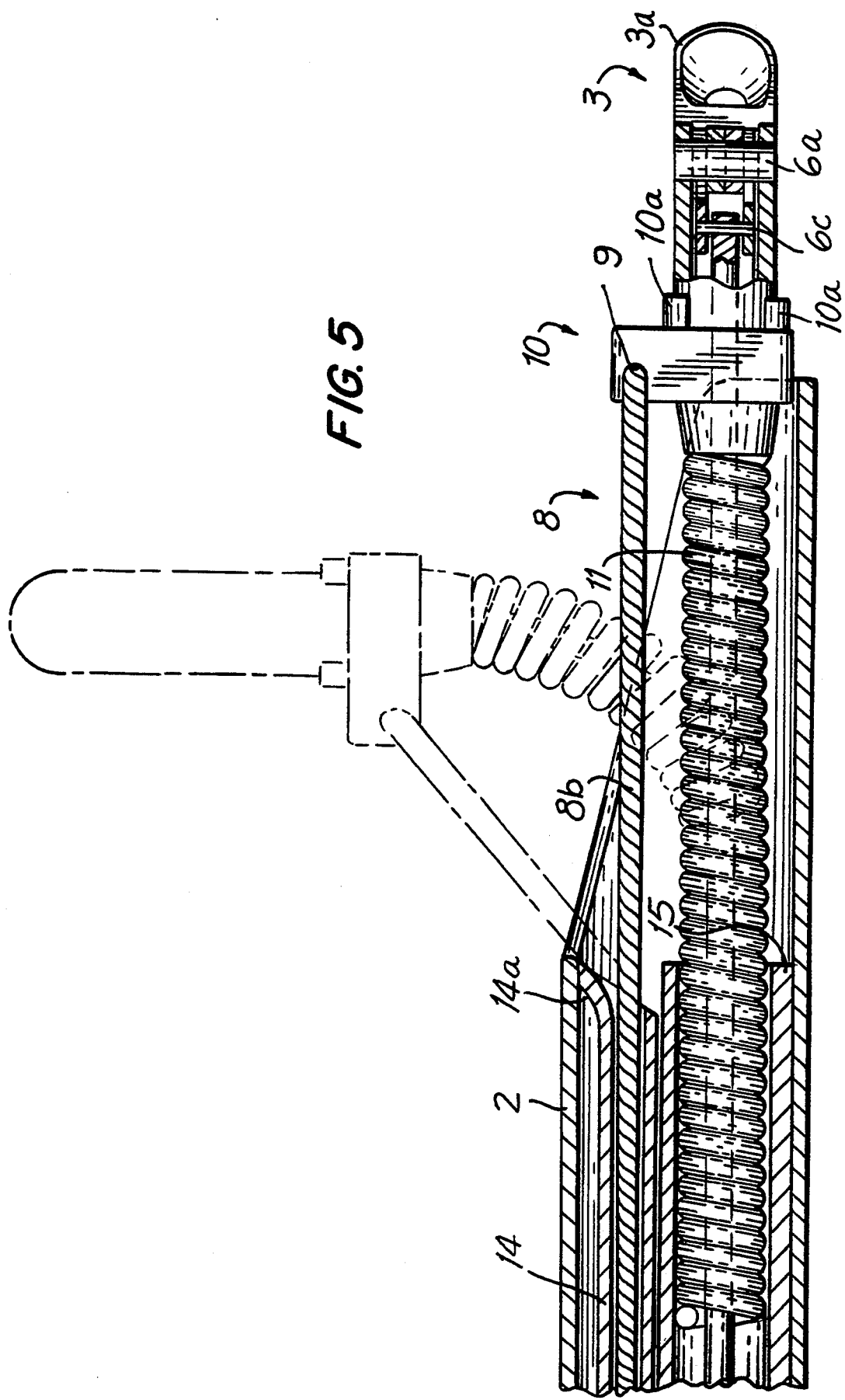

FIG. 5 is a detail elevational view, in section, of the distal end of the forceps of FIG. 1;

FIG. 6 is a detail view, in perspective, of the distal end of the forceps;

FIG. 7 is a detail elevational view, in section, in enlarged scale, of the proximal end of the forceps of FIG. 1;

FIG. 8 is a detail elevational view, in section, of the actuator for the jaws of the forceps of FIG. 1.

Figure 2:
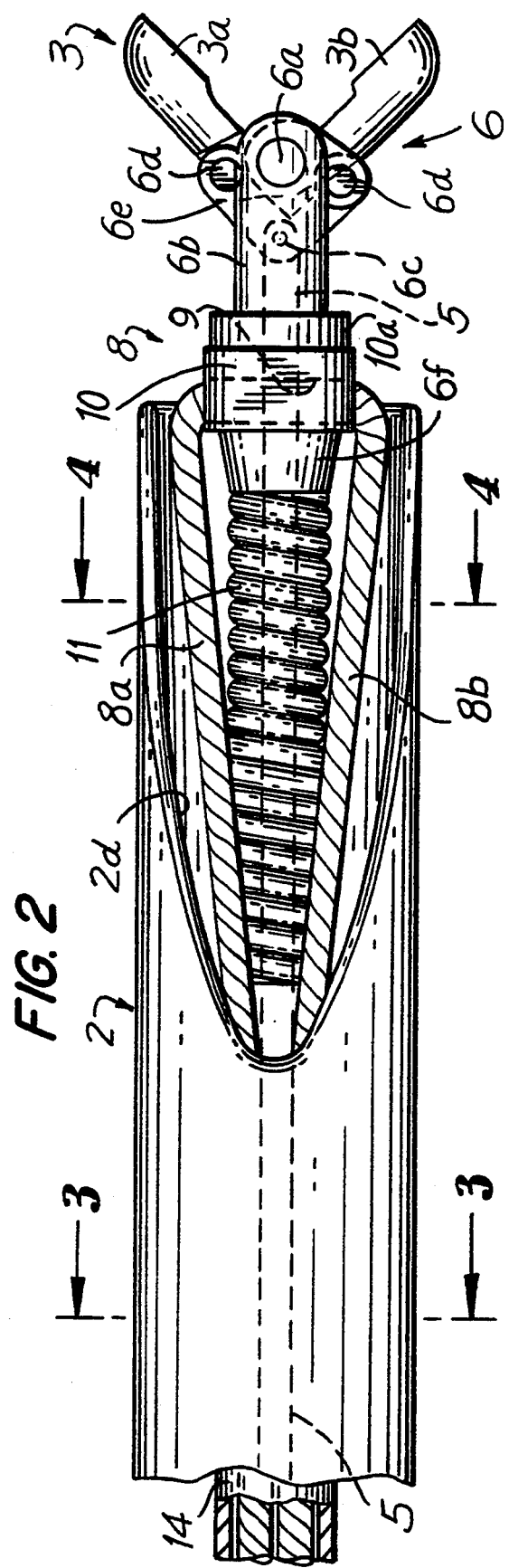
FIG. 2 is a detail top plan view, in enlarged scale, partly in section, of the distal end of the forceps of FIG. 1.

Referring to FIG. 1, the forceps 1 has an elongated tubular housing 2 of a length which is nearly the length of the forceps 1, a pair of forceps jaws 3 at the distal end 2a of housing 2 and a pair of normally open handles 4a, 4b at the proximal end 2b of housing 2. Movable handle 4a is connected to one end of a cable 5, while the other end of cable 5 is connected to a pantograph linkage 6 (FIG. 2), which in turn is connected to jaws 3. Closing and opening the handles 4a, 4b opens and closes the jaws 3, respectively, via cable 5 and linkage 6, as is conventional.

Actuator 7 is located at the proximal end 2b of housing 2. While shown as pivotally mounted on fixed handle 4b, actuator 7 can, if desired, be mounted instead on the proximal end 2b of housing 2. Cable 8 is connected to actuator 7 and is looped through bore 9 in collar 10. As presently preferred, lengths 8a, 8b of cable 8 extend from collar 10 through the interior 2c of housing 2 and are fastened to the underside of actuator 7, as shown in FIG. 8. In the embodiment of the forceps 1 shown in the drawings, collar 10 is secured, as by brazing, to linkage 6 and hence to jaws 3 (FIG. 6). However, the linkage 6 may include an integral portion (not shown) having a bore for receiving the loop 8c of cable 8. Alternatively, collar 10 can be rotatably linked to cable 8 by other means, such as by connecting a loop (not shown) at the distal end of cable 8 to a post (not shown) carried by collar 10.

It is presently preferred to locate cable 8 within sleeve 14, which is in turn located within housing 2. However, sleeve 14 can also be located on the outside of housing 2 (not shown) with the cable 8 thus passing through sleeve 14 externally of housing 2. Furthermore, sleeve 14 can even be omitted entirely, with the cable 8 simply being located inside or outside of housing 2.

Depression of the actuator 7 to the dotted line position shown in FIG. 1, as by thumb pressure, will apply a swinging force to collar 10 via cable 8 and hence will swing the jaws 3 from the normal position shown in FIG. 5, wherein the jaws are parallel to the longitudinal axis of housing 2, to the dotted line position (FIG. 5), wherein the jaws 3 are transverse to the longitudinal axis of housing 2. Spring 11, which is in compression, urges the jaws 3 to return to the normal position.

In a preferred embodiment of the invention, a suction conduit 12 having an internal valve 13 communicates with the interior 2c of housing 2 as will be described in detail hereinafter. When conduit 12 is connected to a source of suction, tissue near the distal end of the forceps will be pulled by suction to the jaws 3, and smaller bits of tissue removed by jaws 3 can be aspirated from the surgical site through the interior 2c of housing 2. Valve 13 can be operated to control the degree of suction or to disconnect the interior 2c of housing 2 from the source of suction, as desired. If desired, the forceps 1 can be made without suction conduit 12 and valve 13.

Jaws 3 may take the form of any useful tool. As shown, jaws 3 comprise forceps cups 3a, 3b, which may have serrated edges (not shown) if desired. Other useful tools include scissors, graspers and the like.

It is presently preferred to use a pantograph linkage 6 (FIG. 2) comprising stationary pivot 6a carried by stationary arms 6b (FIG. 6), movable pivot 6c connected to the cable 5 (FIG. 5) and movable pivots 6d that pivotally connect jaws 3a, 3b to the movable linking members 6e. The use of a pantograph linkage to connect forceps jaws to a pull cable is conventional; other linkages may also be used.

As best seen in FIG. 6, arms 6b extend from a fitting having a frustoconical portion 6f that is brazed or otherwise fastened to spring 11. Collar 10 has opposed arcuate portions 10a and opposed tabs 10b that are bent into the slot formed between arms 6b to restrain rotational movement of the collar 10 and to add axial strength.

Spring 11 is press-fit into or is otherwise fastened to sleeve 15 (FIG. 6). As stated above, spring 11 is in compression. Sleeve 14 is welded to sleeve 15 by fillet 16 (FIG. 3). If desired, however, sleeve 15 can be omitted, in which case cable 5 will simply pass through housing 2. If sleeve 15 is omitted, the proximal end of spring 11 may be tack welded or otherwise fastened to housing 2 so that the proximal end of spring 11 is fixed in position relative to housing 2.

To facilitate the swinging of jaws 3 by cable 8, the distal end 2a of housing 2 is provided with a truncated arc 2d (FIGS. 2 and 6), while the distal end of sleeve 14 terminates in an upturned flange 14a formed by bending sleeve 14 upwardly and cutting the bent portion at an angle. Flange 14a may be brazed or otherwise fastened to the interior of housing 2. Flange 14a and truncated arc 2d are proportioned to permit jaws 2 to swing through the desired angle, such as up to about 135°.

Referring to FIG. 7, suction conduit 12 is received in and fastened to fitting 20, as by brazing. The proximal end of housing 2 is then inserted into bore 21, with sleeves 14 and 15 projecting through bores 21 and 22 and beyond fitting 20. Sleeve 14 is provided at its proximal end with an upturned portion 14b through which project cable portions 8a, 8b. Bore 22 is provided with a notch portion 23 to accommodate upturned portion 14b.

Handle 4b is inserted into bore 22 with sleeve 15 passing through bore 30 in handle 4b and upturned portion 14b being received by the notch 31. Handle 4b is fastened to fitting 20, as by brazing, while upturned portion 14b and the proximal end of sleeve 15, which projects slightly beyond handle 4b, are fastened to handle 4b, also as by brazing. Cables 8 and 5 are threaded through their sleeves 14 and 15 and fastened to actuator 7 and handle 4a, respectively.

In operation, a cannula (not shown) is inserted into the disc using the procedure described in U.S. Pat. No. 4,573,448. At an appropriate time during the procedure, the forceps 1 is inserted through the cannula and into the disc. Forceps 1 is advanced to the desired position and operated to grasp and remove tissue by means of jaws 3. Forceps 1 can be rotated about its longitudinal axis, if desired. Where tissue to be removed is at a position remote from the longitudinal axis, and hence not accessible to jaws 3 when in their normal position, actuator 7 can be depressed by the thumb of the same hand holding the handles 4a, 4b to swing jaws 3 through the desired angle to reach the remote tissue site.

Actuator 7 can be slightly depressed or fully depressed to the position shown in dotted line in FIG. 1 depending on the desired angle through which the jaws are to be swung. Thereafter, the surgeon will maintain the actuator 7 in place to thereby maintain the jaws 3 in place. Handles 4a, 4b are then operated to open and close the jaws. Thereafter, jaws 3 can be moved to another position by operation of actuator 7 and/or by rotating and/or sliding forceps 1 within the cannula.

We claim:

1. A forceps apparatus comprising:
   (a) an elongated rigid tubular housing having a bore with a longitudinal axis, the housing having proximal and distal end and a length which is nearly the entire length of the forceps apparatus portions;
   (b) a pair of jaws extending beyond the distal end portion of the elongated tubular housing;
   (c) manually operable handle means positioned at the proximal end portion of said housing for operating said jaws, each handle having a portion that is spaced laterally away from the housing's longitudinal axis;
   (d) linkage means extending through said bore between said handle means and said jaws for transmitting force between said handle means and said jaws during the operation of opening or closing the jaws;
   (e) cable means positioned within the housing bore for moving said jaws from a first position wherein said jaws extend in a direction parallel to and generally aligned with the longitudinal axis of said housing bore to a second position wherein said jaws are positioned laterally away from said longitudinal axis, a cable end portion being permanently attached to the jaws for movement therewith;
   (f) a manually operable actuator means positioned at the proximal end of said housing and connected to said cable means for operating said cable means;
   (g) said handle means and actuator means being arranged for operation by the hands of a user; and
   (h) said linkage means including biasing means rigidly supported at the distal end portion of the housing, extending from the bore for returning the jaws to a position aligned with the longitudinal axis of the housing bore.

2. The forceps according to claim 1, wherein said cable means extend from said actuator through said housing to said forceps jaws.

3. The forceps according to claim 1, wherein conduit means are provided in communication with the interior of said housing for applying suction to said housing, said housing being open at said distal end.

4. A deflecting forceps apparatus comprising:
   (a) a pair of handles pivotally connected to one another and pivotally movable relative to one another between open and closed positions;
   (b) an elongated rigid tubular housing with proximal and distal end and a length which is nearly the entire length of the forceps apparatus portions, a bore having a longitudinal axis and a length which is nearly the entire length of the forceps apparatus, said housing being fixed at its proximal end portion to and extending from one of said handles and terminating in the distal end portion;
   (c) a pair of jaws positioned at said distal free end portion;
   (d) linking means having a longitudinally extending axis extending through said housing bore, the linking means having a proximal and a distal end, said linking means being connected at its proximal end to at least one of said handles, and at its distal end being connected to said jaws;
   (e) said linking means having means for moving the jaws between open and closed positions responsive to a movement of said handles relative to one another by the user's hand between said positions to thereby operate said jaws;
   (f) an actuator cable means having a longitudinally extending axis parallel to said housing bore, said actuator cable means having a proximal and a distal end; and (g) actuator means pivotally mounted at the proximal end portion of said housing and connected to the proximal end of said actuator cable means, the distal end of said actuator cable means being operatively associated with said forceps jaws such that manually pivoting said actuator means causes said actuator cable means to swing said forceps jaws from a first aligned position wherein said forceps jaws are parallel to the longitudinal axis of said housing bore to a second offset position wherein said forceps jaws are transverse to said longitudinal axis; and (h) wherein said linking means includes a spring urging said forceps jaws to said first position, said spring has a distal end connected to said forceps jaws for movement therewith as said forceps jaws swing between said positions and a proximal end that is fixed with respect to said housing.

5. The deflecting forceps according to claim 4, wherein said distal end portion of said tubular housing has a truncated arcuate opening to facilitate the swinging of said forceps jaws from said first position to said second position.

6. The deflecting forceps according to claim 4, wherein a conduit means is secured to said tubular housing in communication with the interior thereof for applying suction to said housing, said housing being open at the distal end.

7. The deflecting forceps according to claim 4, wherein said forceps jaws linking means comprises a sleeve in said housing in fixed relation thereto, a pantograph linkage connected to the proximal end of said forceps jaws and a forceps jaws cable within said sleeve having its distal end connected to said pantograph linkage and its proximal end connected to said other handle.

8. The deflecting forceps according to claim 4, wherein said forceps jaws linkage means comprises a sleeve in said housing in fixed relation thereto, said proximal end of said spring being fastened to the distal end of said sleeve, and a forceps jaw cable within said sleeve and said spring having its distal end operatively associated with said forceps jaws and its proximal end connected to said movable handle.

9. The deflecting forceps according to claim 4, wherein an actuator cable sleeve is provided in said housing in fixed relation thereto, said actuator cable means passing through said actuator cable sleeve.

10. A forceps apparatus comprising:

(a) an elongated rigid tubular housing having a bore with a longitudinal linear axis, the housing having proximal and distal end and a length which is nearly the entire length of the forceps apparatus portions;

(b) a pair of jaws extending beyond the bore at the distal end portion of the elongated tubular housing;

(c) a pair of manually operable handles positioned at the proximal end portion of said housing for operating said jaws, at least one of said handles rigidly connected to the housing proximal end portion, and one of the handles being movable relative to the other handle for operating said jaws responsive to said movement, each handle having a portion that is spaced laterally away from the housing's longitudinal linear axis;

(d) a linkage member extending through said bore between said handles and said jaws for transmitting force between said handles and said jaws during the operation of opening or closing the jaws wherein the jaws open and close when the handles are moved relative to one another;

(e) a cable positioned within the housing bore for moving said jaws from a first position wherein said jaws extend in a direction parallel to and generally aligned with the longitudinal axis of said housing bore to a second position wherein said Jaws are positioned laterally away from said longitudinal axis, a cable end portion being permanently attached to the jaws for movement therewith;

(f) the jaws being supported upon a coil spring rigidly supported at the distal end portion of the housing and extending from the bore for returning the jaws to a position aligned with the longitudinal axis of the housing bore, wherein tension applied to the cable flexes the coil spring to move the jaws laterally away from the bore longitudinal linear axis; and (g) a manually operable actuator positioned at the proximal end portion of said housing and connected to said cable for operating said cable to flex the spring and move the jaws laterally.

* * * * *